(12) United States Patent
Ehlgen et al.

(10) Patent No.: US 9,676,321 B2
(45) Date of Patent: *Jun. 13, 2017

(54) METHOD AND APPARATUS FOR RECOGNIZING AN INTENSITY OF AN AEROSOL IN A FIELD OF VISION OF A CAMERA ON A VEHICLE

(75) Inventors: Tobias Ehlgen, Ravensburg (DE); Sebastian Van Staa, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 877 days.

This patent is subject to a terminal disclaimer.

(21) Appl. No.: 14/114,151

(22) PCT Filed: Apr. 20, 2012

(86) PCT No.: PCT/EP2012/057297
§ 371 (c)(1),
(2), (4) Date: Apr. 17, 2014

(87) PCT Pub. No.: WO2012/146543
PCT Pub. Date: Nov. 1, 2012

(65) Prior Publication Data
US 2014/0044312 A1    Feb. 13, 2014

(30) Foreign Application Priority Data
Apr. 28, 2011    (DE) .................. 10 2011 017 649

(51) Int. Cl.
*G06K 9/00* (2006.01)
*B60Q 1/08* (2006.01)
(Continued)

(52) U.S. Cl.
CPC ............ *B60Q 1/085* (2013.01); *B60Q 1/143* (2013.01); *B60Q 1/20* (2013.01); *G01N 21/538* (2013.01);
(Continued)

(58) Field of Classification Search
CPC ...... B60Q 1/143; B60Q 1/085; B60Q 1/1423; G06K 9/00791; G06K 9/4652;
(Continued)

(56) References Cited

U.S. PATENT DOCUMENTS 6,320,176 B1    11/2001 Schofield et al.
6,587,573 B1 *   7/2003 Stam .................. B60Q 1/085
                                                340/930

(Continued)

FOREIGN PATENT DOCUMENTS

| CN | 1751391 A | 3/2006 |
|---|---|---|
| DE | 10 2008 029 256 | 12/2009 |
| DE | 10 2010 002 488 | 9/2011 |
| EP | 17 90 541 | 5/2007 |

OTHER PUBLICATIONS

Stephen M. Metzger, James R. Carr, Jeffrey R. Johnson, Timothy J. Parker, and Mark T. Lemmon, "Techniques for Identifying Dust Devils in Mars Pathfinder Images", IEEE, Transactions on Geoscience and Remote Sensing, vol. 38, No. 2, Mar. 2000, pp. 870-876.*

(Continued)

*Primary Examiner* — Eric Rush
(74) *Attorney, Agent, or Firm* — Norton Rose Fulbright US LLP; Gerard Messina

(57) ABSTRACT

A method for recognizing an intensity of an aerosol in a field of view of a camera of a vehicle includes: reading in image information of an image of the camera, providing a color indicator value for at least one subsection of the image, the color indicator value representing a relation between (i) a first parameter representing a value obtained with application of a first color filter to the image information in the subsection, and (ii) a second parameter representing a value obtained without application of a color filter, or with application of a second color filter differing from the first color filter, and providing a gradient indicator value representing (Continued)

a brightness difference of a different image region of the image, an aerosol intensity value being determined using the color indicator and the gradient indicator values.

13 Claims, 3 Drawing Sheets

(51) Int. Cl.
  *B60Q 1/14* (2006.01)
  *B60Q 1/20* (2006.01)
  *G01N 21/53* (2006.01)
  *G06T 7/00* (2017.01)
  *G06T 7/44* (2017.01)
  *G06T 7/90* (2017.01)

(52) U.S. Cl.
  CPC ............ *G06K 9/00791* (2013.01); *G06T 7/00* (2013.01); *G06T 7/44* (2017.01); *G06T 7/90* (2017.01); *B60Q 2300/312* (2013.01); *G06T 2207/10016* (2013.01); *G06T 2207/10024* (2013.01); *G06T 2207/30192* (2013.01); *G06T 2207/30252* (2013.01)

(58) Field of Classification Search
  CPC ...... G01N 21/538; G01N 21/25; G06T 7/403; G06T 7/408; G06T 7/90; G06T 2207/30248; G06T 2207/30252; B60R 2300/8053
  USPC .......................... 382/104, 162, 260, 100, 165
  See application file for complete search history.

(56) References Cited

U.S. PATENT DOCUMENTS

| | | | |
|---|---|---|---|
| 7,693,629 B2* | 4/2010 | Kawasaki | B60W 40/072 348/148 |
| 7,983,447 B2 | 7/2011 | Higuchi et al. | |
| 9,260,052 B2* | 2/2016 | Ehlgen | G06T 7/403 |
| 2004/0143380 A1* | 7/2004 | Stam | B60Q 1/085 701/36 |
| 2005/0035926 A1* | 2/2005 | Takenaga | G06K 9/00791 345/8 |
| 2005/0270537 A1* | 12/2005 | Mian | G01N 21/538 356/437 |
| 2006/0177098 A1* | 8/2006 | Stam | B60Q 1/085 382/104 |
| 2007/0031006 A1 | 2/2007 | Leleve et al. | |
| 2008/0007429 A1* | 1/2008 | Kawasaki | G01N 21/538 340/905 |
| 2008/0170754 A1* | 7/2008 | Kawasaki | G06K 9/00825 382/104 |
| 2010/0157614 A1* | 6/2010 | Hue | B60Q 1/085 362/466 |
| 2010/0172542 A1* | 7/2010 | Stein | G06K 9/00798 382/103 |
| 2011/0135200 A1* | 6/2011 | Chen | G06T 5/003 382/167 |

OTHER PUBLICATIONS

International Search Report for PCT/EP2012/057297, dated Jul. 20, 2012.

\* cited by examiner

METHOD AND APPARATUS FOR RECOGNIZING AN INTENSITY OF AN AEROSOL IN A FIELD OF VISION OF A CAMERA ON A VEHICLE

BACKGROUND OF THE INVENTION

1. Field of the Invention

The present invention relates to a method for recognizing an intensity of an aerosol in a field of view of a camera of a vehicle, to a corresponding device, and to a corresponding computer program product.

2. Description of the Related Art

Conventional driver assistance systems often offer no recognition, or very inadequate recognition, of meteorological phenomena when underway in the vehicle, such as the occurrence of fog or smoke in front of the vehicle. In particular at night or in conditions of darkness, when the headlamps are switched on during travel this can result in dangerous travel situations, for example if, when entering a fog bank, the illumination is set too high and the driver is thus blinded by the strong reflection of light from the aerosol droplets that form the fog.

DE 102010002488 (unpublished at the time of filing of the present application) proposes a spectroscopic method for recognizing, inter alia, fog.

BRIEF SUMMARY OF THE INVENTION

Against this background, the present invention presents a method for recognizing an intensity of an aerosol in a field of view of a camera of a vehicle, and a device that uses this method, as well as, finally, a corresponding computer program product.

The present invention creates a method for recognizing an intensity of an aerosol in a field of view of a camera of a vehicle, the method including the following steps:

reading in of image information of a camera image;

provision of a color indicator value for at least one subsection of the camera image, the color indicator value representing a relation between a first parameter and a second parameter, the first parameter representing a value that is obtained by applying a first color filter to the image information in the subsection, and the second parameter representing a value that is obtained without applying a color filter, or is obtained by applying a second color filter differing from the first color filter to the image information in the subsection, there being further provided in the step of provision a gradient indicator value that represents a brightness difference that can be derived from the image information of a different, in particular adjacent, image region of the camera image; and determination of an aerosol intensity value using the color indicator value and using the gradient indicator value, in order to determine the intensity of the aerosol in the field of view of the camera of the vehicle.

In addition, the present invention creates a device for recognizing an intensity of an aerosol in a field of view of a camera of a vehicle, the device including the following features:

an interface for reading in image information about a camera image;

a unit for providing a color indicator value for at least one subsection of the camera image, the indicator value representing a relation between a first parameter and a second parameter, the first parameter representing a value that is obtained by applying a first color filter to the image information, and the second parameter representing a value that is obtained without applying a color filter, or by applying a second color filter differing from the first color filter, to the image information, a gradient indicator value being further provided in the unit for provision that represents a brightness difference that can be derived from the image information of a different, in particular adjacent, image region of the camera image; and a unit for determining an aerosol intensity value, using the color indicator value and using the gradient indicator value to determine the intensity of the aerosol in the field of view of the camera of the vehicle.

The present invention therefore creates a device that is fashioned to carry out or implement the steps of the method according to the present invention in corresponding devices. The object of the present invention can also be achieved quickly and efficiently by this variant embodiment of the present invention in the form of a device.

In the present context, a device may be understood as an electrical apparatus that processes sensor signals and outputs control signals as a function thereof. The device can have an interface that can be realized as hardware and/or as software. In the case of a hardware realization, the interfaces can for example be part of a so-called system ASIC containing a wide range of functions of the device. However, it is also possible for the interfaces to be made up of separate integrated circuits or to be made up at least partly of discrete components. In a realization as software, the interfaces can be software modules present for example on a microcontroller alongside other software modules.

Also advantageous is a computer program product having program code that can be stored on a machine-readable bearer such as a semiconductor memory device, a hard drive memory device, or an optical memory, and can be used to carry out the method according to one of the above-described specific embodiments when the program is executed on a computer or on a device.

Here, a camera can be understood as a device for optical acquisition, for the visual acquisition of the surrounding environment of the vehicle in a field of view of the camera. An aerosol can be understood for example as a mixture of liquid or solid particles in a gas, such as for example fog, vapor, or smoke, present in the air in the field of vision of the camera of the vehicle. An intensity of an aerosol can for example be understood as a quantity of drops or particles that appear to be present in the field of view of the camera of the vehicle. Image information can be understood as a set of data representing the image recorded by the camera, for example in the form of color or brightness information of individual pixels of the camera image. A subsection of the camera image can be understood as a region of the camera image that includes either the entire camera image or only a part of the camera image. A relation can be understood in general as a mathematical relationship between parameters, such as the formation of a comparison, the formation of a quotient, the formation of a difference, or the like, it being insignificant which of the parameters appears for example in the numerator or in the denominator in the formation of quotient, or which parameter is used as the minuend or as the subtrahend in the formation of a difference. A value obtained by applying a color filter to the image information in the subsection may be understood as a value that represents color information occurring in the subsection of the camera image, a spectral component having however been filtered out or suppressed by the color filter. Thus, the value obtained with application of a color filter does not reproduce the actual color information as seen by the camera in the relevant subsection of the image. The gradient indicator value, which can also be designated the average gradient in a region of the image, is for example the average value of the changes in brightness from one pixel to the next. Here, in the case of a uniform image with little structure (i.e. having small differences between adjacent pixels), a low gradient indicator value or average gradient would be present, which would indicate fog. An aerosol intensity value can be understood as a parameter that represents the occurrent intensity of the aerosol. In addition, it is also conceivable that the value obtained through application of a color filter to the image information in the subsection is obtained by averaging a plurality of individual values of this sort.

The present invention is based on the recognition that through the comparison of at least two values from the subsection of the camera image, in which at least one value was determined with the application of a color filter, a reliable recognition of the intensity of the aerosol is possible. Here, an aerosol intensity value can be obtained (in particular as a scalar quantity) that enables a simple determination of the occurrent aerosol in the field of view in front of the vehicle, for example through a threshold value comparison. In particular, in such a determination of the intensity of the aerosol the fact is exploited that particular spectral portions of light are reflected or absorbed with different strengths by an aerosol drop or particle. Through the comparison or relation formation of two values relating to the same subsection of the camera image but containing differing spectral portions, it can thus be recognized which spectral portions of light are reflected by the aerosol, or by an aerosol drop. Because each aerosol drop is responsible for only a small portion of the overall light reflected to the camera, through the evaluation of the corresponding parameters in the respective subsection an inference can be made as to how much aerosol, or how many aerosol drops or particles, are present in the field of view of the vehicle camera. In addition, the present invention is based on the recognition that the determination of the intensity of the aerosol is advantageously not based only on a single optical feature from the image information; rather, for the determination of the intensity of the aerosol the (brightness) gradient, or a difference of (brightness gradient) gradients in different image regions of the camera image, is also used. The 'intensity' of the aerosol can be calculated for example from a linkage of red suppression and average gradient. Here, the image regions used for the evaluation of the brightness or of the gradient are not necessarily situated in the same subsection from which the parameters for the color intensity value are also taken. Consequently, such an approach permits the intensity of the aerosol to be determined fairly reliably, and solely through the use of simple technical aids such as an optical camera. As a result, additional sensors for determining the aerosol can be omitted, thus reducing vehicle production costs.

In addition, it is advantageous if, according to a specific embodiment of the present invention, in the step of determination the aerosol intensity value is determined through a linear combination, in particular through a weighted linear combination, of the color indicator value and the gradient indicator value. Such a specific embodiment of the present invention offers a mathematical operation, easy to carry out in terms of circuitry or numerically, for determining the intensity of the aerosol; in the case of a weighted linear combination in particular, there is additional flexibility as to with what strengths the two intensity values used are to enter into the determination of the aerosol intensity value.

In addition, in a further specific embodiment of the present invention, in the step of determination, before the determination of the aerosol intensity value the color indicator value can be standardized in a range between color indicator boundary values, and/or the gradient indicator value can be standardized in a range between gradient indicator boundary values. In order to carry out a simple determination of the strength in, or intensity of, the aerosol, it is advantageous to standardize one or both of the values used in the determination of the aerosol intensity value. In particular, the indicators can be mapped (=standardized) in certain ranges onto the interval [0; 1], the value 0 meaning for example "fog" and the value "1" meaning clear visibility, or vice versa. In this way, a costly conversion for the linkage of otherwise different values having different physical units can be omitted. The color indicator boundary values and/or gradient indicator boundary values can for example be known ahead of time, as maximum values that the camera can acquire. For example, these boundary values can be determined in a laboratory setting.

According to an advantageous specific embodiment of the present invention, in the step of provision a color indicator value can be provided for which the first or second color filter is a color filter that filters out red portions in the image information. Such a specific embodiment of the present invention offers the advantage that in particular the evaluation based on reflected red portions is very favorable, because the reflection of red portions in an aerosol, such as fog, varies strongly with the intensity of the aerosol.

In addition, it is favorable if, according to a further specific embodiment of the present invention, in the step of determination an aerosol indicator value is determined that is represented by a scalar. Such a specific embodiment of the present invention offers the advantage that a second scalar quantity, technically easy to process, can specify or indicate the intensity of the aerosol, in particular of the fog. In addition, an easy parametrizability/applicability is possible in the case of a technical reaction to fog that can be carried out by a driver assistance system, because for example only a single scalar need be compared with a threshold value, and a plurality of values/comparisons are to be taken into account or carried out.

According to a further specific embodiment of the present invention, in the step of determination the gradient indicator value can be determined using image information from a central region of the camera image, the gradient indicator value being determined in particular using image information originating from an image segment that, given a division of the camera image into nine non-overlapping image segments, is surrounded by eight of these image segments. Such a specific embodiment of the present invention offers the advantage that, in particular in the central region of the camera image, a brightness difference, or brightness gradient, is substantially more strongly pronounced than in an edge region of the image. The suppression of the red portion is for example particularly strongly pronounced in the center of the image (i.e. in the headlamp light cone); there is no influence on the gradient image. In particular the edge regions of the image are not usually strongly illuminated during travel with switched-on headlamps, so that in order to enable the recognition of even small brightness differences given the presence of an aerosol, to the greatest possible extent a region of the camera image is to be used in which smaller differences are nonetheless easily recognizable due to strong illumination.

According to a further specific embodiment of the present invention, in addition a step of recognition of the presence of an intensity of the aerosol that is critical for roadway traffic in the field of view of the vehicle camera can be provided when the aerosol intensity value stands in a specified relation to a threshold value, for example when the aerosol intensity value is greater than the threshold value. Such a specific embodiment of the present invention offers the advantage of a check that is technically very easy to carry out as to whether an intensity of the aerosol has been reached that is critical for the travel of the vehicle. For example, a critical intensity of the aerosol can be considered to be reached when the view in front of the vehicle is below a specified boundary value. When there is a recognition of an intensity of the aerosol that is critical in this way for roadway traffic or for the travel of the vehicle, for example a warning can be outputted to the driver of the vehicle.

In addition, the present invention also creates a method for controlling a headlamp system of a vehicle, having the following steps:

reading in of an aerosol signal that represents an intensity of the aerosol, recognized according to the steps of a method as described above, in the field of view of the camera of the vehicle; and modification of a radiation of light in a region of illumination in front of the vehicle by the headlamp system, in response to the aerosol signal.

Here, a modification can be understood as not merely the radiation of light itself, but rather also as a modification of parameters for controlling the light radiation, such as a modification of the switchover time between high beams and low beams, or a modification of the direction of a radiation of light given a system of floating headlamp range regulation. The modification of the light radiation thus relates to a general modification or parametrization in the controlling of the illumination of the vehicle by the headlamp system. Such a specific embodiment of the present invention offers the advantage of an immediate supporting of the driver given the presence of aerosol in the field of view of the vehicle camera, in which for example the direction of the light radiated by the headlamps is immediately further lowered in the direction of the roadway in order to avoid blinding the driver. If the driver knows that, starting from a particular intensity of the aerosol in the air in front of the vehicle, the driver assistance system will automatically engage and is capable of correspondingly adapting the light radiation, driving can still take place with an optimal illumination of the vehicle, even with low intensity of the aerosol in the field of view of the vehicle camera.

According to a further specific embodiment of the present invention, in the step of modification a modification of a light radiation parameter can be determined as a function of the time of the presence of the aerosol, in particular the presence of a specified minimum intensity of the aerosol. A light radiation parameter can be understood for example as a debounce time (i.e. a time until the beginning of an increasing of the illuminated range), a speed, or a curve by which the illuminated range is increased, an illumination height up to which the headlamps emanate maximum light, or a similar parameter that can be set by an illumination system of the vehicle. Such a specific embodiment of the present invention offers the advantage that a very flexible device is possible for regulating the illuminated range as a function of a time during which a particular determined intensity of an aerosol is present. For example, when traveling through a foggy stretch, it can be recognized that travel has to take place through a high density of fog, or a long stretch in fog having a particular minimum density, so that there is a high probability that, after a recognition that the intensity of the fog has fallen below a given level, travel through a fog bank will again take place after a short time. In this situation, it can be very helpful if, from a modification of the light radiation by the illumination device, waiting then takes place for a longer time span (i.e. a longer debounce time) to find out whether travel through another fog bank having the high intensity will in fact take place, so that this would again lead to a lowering of the beams, or a further modification of the light radiation to the preceding state of illumination.

In addition, it is advantageous if, according to a further specific embodiment of the present invention, in the step of modification a light distribution is modified given an activated light radiation monitoring as a function of the recognized intensity of the aerosol. Such a specific embodiment of the present invention enables a very flexible device for regulating the illumination range as a function of an intensity of the aerosol, such as fog. In this way, the illumination range can be set for example as a function of the actually recognized intensity of the aerosol.

According to a further specific embodiment of the present invention, in the step of modification a modification of a light radiation parameter for a light output by the headlamp system of the vehicle can be changed between different states of illumination. Such a specific embodiment of the present invention offers the advantage that for example a switching of the headlamp system into different states of illumination (e.g. low beams or high beams) is very easily possible. For example, from a set of predefined illumination states, that state of illumination can be selected that is appropriate for the particular situation at that moment. In addition, such a specific embodiment of the present invention offers the advantage that, for example when traveling through fog, when repeated patches of fog occur the changeover from low beams to high beams does not take place too quickly, so that the driver is then not irritated, due to the omission of such a rapid change.

DETAILED DESCRIPTION OF THE INVENTION

Figure 1:
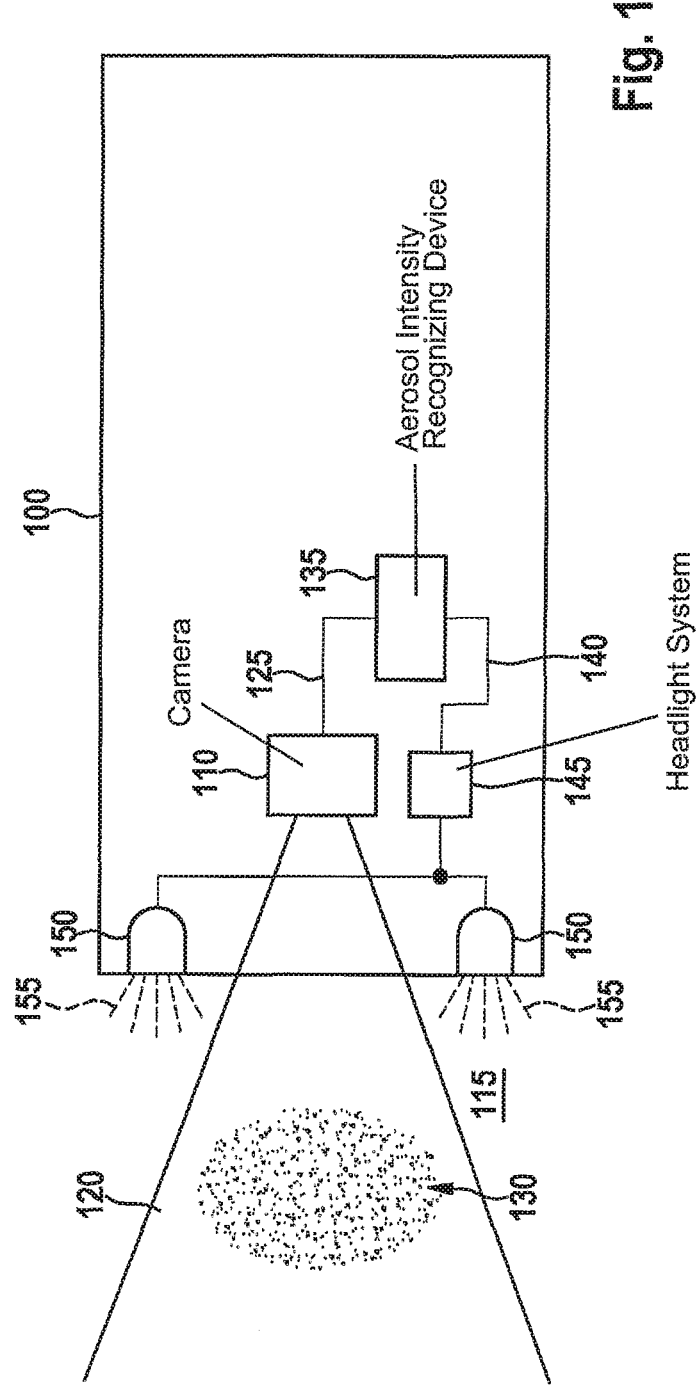
FIG. 1 shows a schematic diagram of a vehicle in which an exemplary embodiment of the present invention is used.

In the following description of preferred exemplary embodiments of the present invention, identical or similar reference characters are used for elements shown in the various Figures and having similar function, and a repeated description of these elements is omitted.

FIG. 1 shows a schematic diagram of a vehicle 100 containing an exemplary embodiment of the present invention. Vehicle 100 has a camera 110 for acquiring a surrounding environment 115 of the vehicle in a field of view 120 of camera 110, and for providing a corresponding camera image 125. Field of view 120 can in particular be a region in front of vehicle 100. An aerosol 130 whose intensity is to be recognized is contained in field of view 120. Camera image 125 is supplied to a device 135 that is fashioned for recognizing the intensity of the aerosol in the field of view of the camera of the vehicle. The precise functioning of device 135 is explained in more detail in the following. If it is now for example recognized that the intensity of aerosol 130 is greater than a specified threshold value, an aerosol signal 140 is generated and is outputted to a headlamp control system 145. In response to aerosol signal 140, there takes place a change in the controlling of the radiation of light by headlamp control system 145, for example in such a way that headlamps 150 of the vehicle are controlled in such a way that light 155 emanated by headlamps 150 is directed at a steeper angle to the roadway on which vehicle 100 is traveling. In this way it can be prevented that light 155 emanated by headlamps 150 is reflected by the aerosol 130, which is situated mostly in the immediate vicinity of vehicle 100, blinding the driver. Headlamp control system 145 can also be present in the form of a system for floating headlamp range regulation. In this context, a pivoting of the headlamps can take place in order to deflect the light beam. However, modern control systems also have a large number of movable mirror elements for reflecting a light beam in a modifiable desired direction, or include a system of small movable individual light sources, through whose displacement (i.e. movement) an illumination of the region in front of the vehicle can be realized in almost any fashion. Such modern systems for floating headlamp range regulation can also be understood as headlamp control system 145; in this case, rather than a changeover of the light emanation only in steps (such as e.g. high beams and low beams), almost continuous modification can take place within a specified illumination region.

Figure 2:
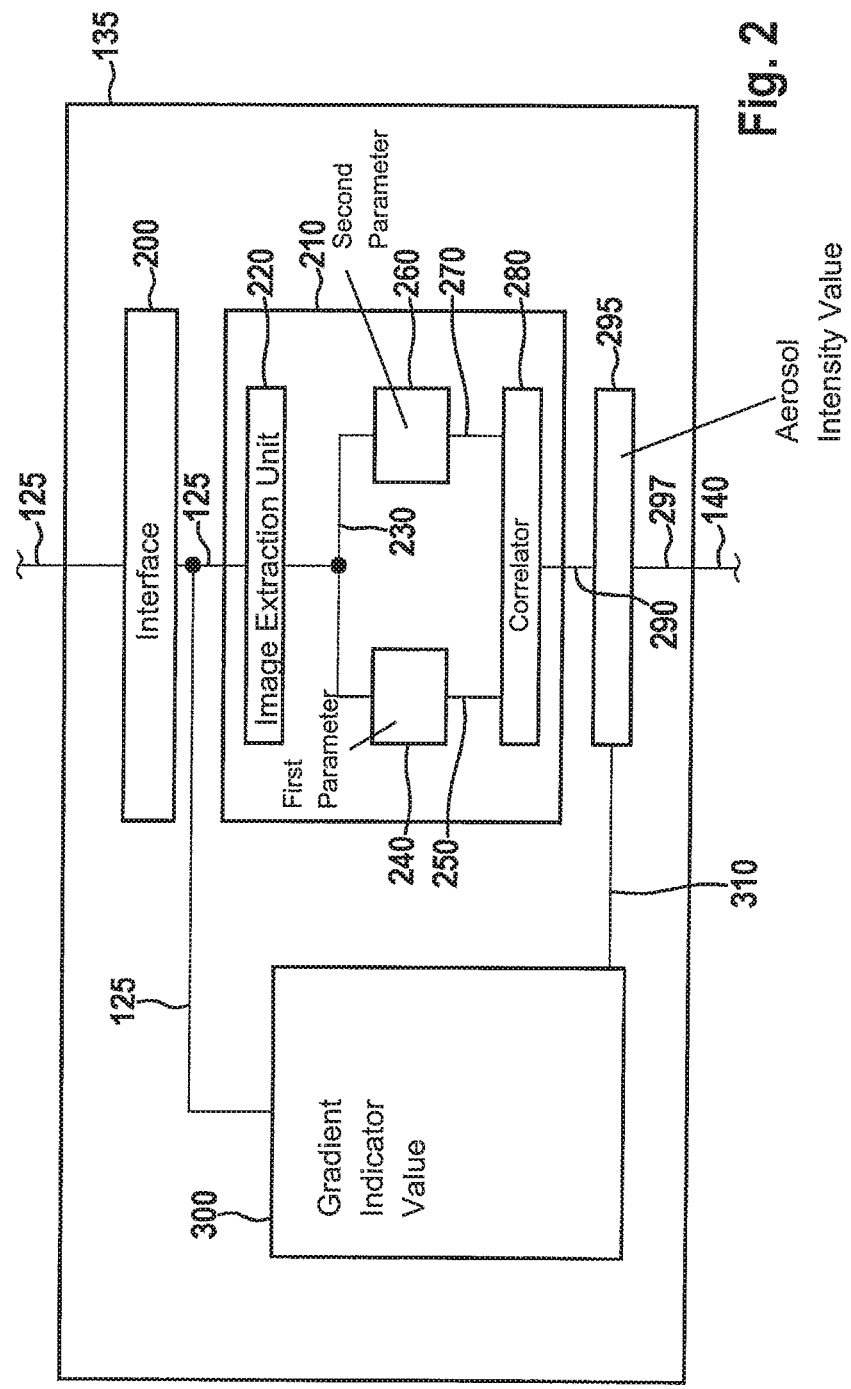
FIG. 2 shows a schematic diagram of a device for recognizing an intensity of an aerosol in a field of view of a camera of a vehicle according to an exemplary embodiment of the present invention, for a flow diagram of an exemplary embodiment of the present invention.

FIG. 2 shows a schematic diagram of device 135 shown schematically in FIG. 1 for recognizing an intensity of an aerosol in a field of view of a camera of the vehicle. Device 135 has an interface 200 for reading in image information of image 125 of camera 110. This image information is read in for example in the form of a digital data file representing the images recorded by camera 110. For reasons of simplicity, the image provided by camera 110 can be read in directly, without previously carrying out various image processing steps. In addition, device 135 includes a unit 210 for providing a color indicator value. This unit 210 includes a unit 220 in which a subsection 230 of image 125 that was received by interface 200 is extracted. A subsection 230 of image 125 can be understood here as a spatially smaller region of the image of camera 110 that nonetheless includes all information of image 125 in this smaller spatial partial area of image 125. Such a subsection 230 contains in particular a region of camera image 125 that is of particular interest for the travel of the vehicle. For example, during travel through a curve to the left, subsection 230 can be extracted from a left region of camera image 125, because this region contains substantially more important information for the safe travel of the vehicle then does for example the image information in the right region of camera image 125. The selected subsection 230 is then supplied to a unit 240 for determining a first parameter 250, and to a unit 260 for determining a second parameter 270. In unit 240 for determining first parameter 250, subsection 230 of image 125 of the camera is subjected to a first color filtering, in which for example red portions contained in subsection 230 are suppressed, i.e. filtered out or strongly attenuated. First parameter 250 thus represents a subsection 230 of image 125 in which the image information, with regard to the red spectral portion of the image, does not agree with the image information recorded by camera 110 in this subsection 230. In unit 260 for determining second parameter 270, subsection 230 of image 125 can be subjected to a second color filtering, such as a filtering of blue spectral components, in order to obtain second parameter 270. Also in unit 260, for the determination of second parameter 270 a spectral filtering can be omitted, so that parameter 270 corresponds to the image information of subsection 230.

First parameter 250 and second parameter 270 are set into relation with one another in a unit 280 in order to determine color indicator value 290. Here, for example a quotient is formed of first parameter 250 and second parameter 270 in order to obtain color indicator value 290. This color indicator value 290 is for example used in a unit 295 in order to determine aerosol intensity value 297, which represents the intensity of aerosol 130 in a field of view 120 of camera 110 of vehicle 100. This aerosol intensity value 297 is then for example transmitted, as aerosol signal 140, to headlamp control system 145.

Through the evaluation, with regard to different spectral portions, of the reflective properties of objects in field of view 120 of camera 110 in front of the vehicle, it can be recognized very well whether an aerosol 130 is present in field of view 120, and with what intensity this aerosol 130 is present in field of view 120 of camera 120. The use of the image of camera 110 thus makes it possible to avoid the use of additional sensors specifically for the recognition of an aerosol 130 in front of vehicle 100, which on the one hand reduces the system complexity of vehicle 100, and in addition avoids additional costs in the production of vehicle 100.

In addition, device 135 includes for example optional unit 300, which provides a gradient indicator value 310. This unit 300 can compare, or set into relation with one another, a brightness or a gradient (relating to the brightness) of two different image regions, for example two different, in particular adjacent, pixels of image 125 of camera 110, and in this way can generate and provide gradient indicator value 310. Gradient indicator value 310 can for example correspond to a gradient that represents the difference of the brightness of the two different image regions. Gradient indicator value 310 is then further used by unit 295 for this issuing of aerosol intensity value 297. In the selection of the image regions used to determine gradient indicator value 310, it is particularly favorable if a central region of the image of the camera is used, because in this region the maximum light strength of the light 155 emanated by the two headlamps 150 is to be expected. In the case of a maximum light star, a brightness difference can also be determined with the greatest possible degree of precision. In particular, here, given a division of camera image 125 into nine equally large non-overlapping image segments, the center image segment, i.e. the image segment surrounded by eight of these image segments, can be used to determine gradient indicator value 310. In order in addition to avoid errors in the determination of the gradient indicator value, averaging can also be carried out of the brightness differences of the individual image regions in the image segment under consideration.

Through the use of the gradient indicator value, which represents different brightnesses in different image regions, the recognition of the intensity of the aerosol can in addition be further improved by taking into account a second physical parameter that is not a function of spectral back-scatter properties of the aerosol drops.

Figure 3:
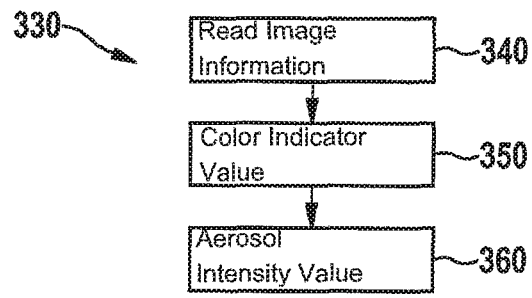
FIG. 3 shows a flow diagram of an exemplary embodiment of the present invention as a method.

FIG. 3 shows a flow diagram of an exemplary embodiment of the present invention as method 330 for recognizing an intensity of an aerosol in a field of view of a camera of a vehicle. The method includes a step of reading in 310 of image information of an image of the camera. In addition, method 330 includes a step of provision 350 of a color indicator value for at least one subsection of the image of the camera, the color indicator value representing a relation between a first parameter and a second parameter, the first parameter representing a value that is obtained with application of a first color filter to the image information in the subsection, and the second parameter representing a value obtained without application of a color filter, or with application of a second color filter differing from the first color filter, to the image information in the subsection, a gradient indicator value further being provided, in the step of provision, that represents a brightness difference that can be derived from the image information of a different, in particular adjacent, image region of the image of the camera. Finally, method 330 includes a step of determination 360 of an aerosol intensity value using the color indicator value and using the gradient indicator value in order to determine the intensity of the aerosol in the field of view of the camera of the vehicle.

In particular, the present invention can be used to measure fog intensity in the context of a camera-based light controlling. Additional sensors for recognizing fog can then be avoided in the vehicle, thus saving costs. The recognition of an aerosol in the environment around the vehicle, in particular fog, takes place here in video-based fashion. The determination of the fog density is determined by evaluating one or more different fog indicators that are present, extracted from the image information of the camera image.

It is advantageous that, in particular, the strength of the measured aerosol or fog can be quantified by a single scalar as aerosol intensity value.

In order to determine such an aerosol intensity value,
color indicator value a is used, which in particular represents a suppression of the average red pixels in a region of interest (i.e., in a region of the image of the camera, that); and
gradient indicator value b is used, which represents an average gradient in the center nonant of the image, a nonant of the image being understood as a segment that is one-ninth of the image of the camera, similar to a quadrant, which designates one-fourth of a whole.

Through a linear combination of these indicator values, the (for example scalar) aerosol intensity value c can be calculated as a further indicator quantifying the intensity of the detected fog.

If color indicator value a has a value from value range a1 to a2, a transformation formula $$\frac{a - a_1}{a_2 - a_1}$$

can be applied in order to map, or standardize, it to the value range between 0 and 1. Correspondingly, gradient indicator value b, which for example likewise assumes values from the value range b1 to b2, can be mapped, or standardized, to the value range between 0 and 1 through the application of transformation formula $$\frac{b - b_1}{b_2 - b_1}$$

In this way, a linkage of different values (having different physical units) is easily possible. In addition, through the standardization of the indicator values given known boundary values, it is also possible to obtain an aerosol intensity value that lies in a value range between 0 and 1, so that the aerosol intensity value also very easily enables an estimation as to how high the relative aerosol concentration is in the field of view of the vehicle camera. In particular, the indicators in certain regions can be mapped (=standardized) onto the interval [0; 1], the value 0 for example meaning "fog" and the value "1" meaning clear visibility, or vice versa.

Here, the relation between color indicator value a and gradient indicator value b for determining an aerosol intensity value c can be expressed in the form of an equation as follows:

$$c = \gamma * \frac{a - a_1}{a_2 - a_1} * (1 - \gamma) \frac{b - b_1}{b_2 - b_1},$$

it being possible to set, via parameter $\gamma = [0 \ldots 1]$, a weighting of the indicators for fine adjustment or fine tuning of the aerosol intensity recognition.

The fog density indicator, or aerosol intensity value c, calculated in this way with the value range between 0 and 1 is therefore a measure of the strength or intensity of the detected fog.

In the case of indicators, such as the color indicator value or the gradient indicator value, for which a decrease in the absolute value is correlated with a higher fog density, the sign is correspondingly to be negated.

Fog density indicator c calculated in this way with value range between 0 and 1 is then for example compared with a threshold value, through which comparison a decision can be made about the intensity or strength of the fog, in order for example to lower the high beams so that the driver is not blinded.

The determination or recognition of the intensity of the aerosol or fog in the environment around the vehicle can be used for various driver assistance applications. For example, in an application of the presently described approach in the high beam assist mechanism of the vehicle, when fog is recognized the headlamps of the vehicle can automatically be switched to low-beam operation in order to avoid blinding the driver as a result of the reflection of the light of the headlamps of the vehicle. In order to avoid a cyclical switching between high beams and low beams, after the fog indication is no longer present a certain period of time should be allowed to pass before switching back to high beams. This time can be selected as a function of the previously detected fog intensity. That is, if heavy fog has been detected, a longer time is allowed to pass than in the case of lighter fog. In addition, besides the aerosol or fog intensity, the duration during which the aerosol or fog is recognized can also be used as a parameter for prolonging the waiting time before switching from low beams to high beams.

Figure 4:
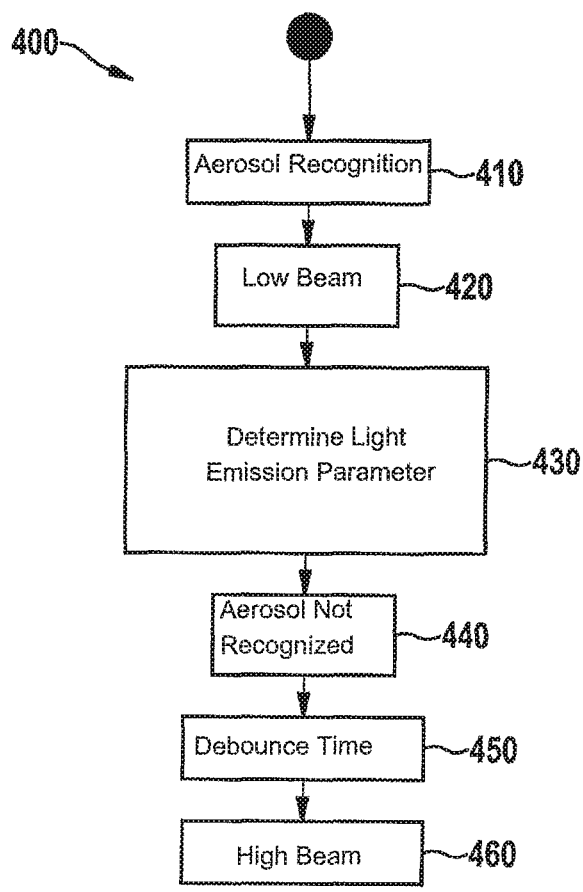
FIG. 4 shows a flow diagram of a further exemplary embodiment of the present invention as a method.

FIG. 4 shows a flow diagram of a further exemplary embodiment for the application of the method according to the present invention, the flow diagram including a modification of the light emanation by the headlamps of the vehicle. First, in a step 410 fog is recognized as an aerosol. In a following step 420, the low beams are activated in order to give the driver an improved view of the roadway. In a further, subsequent step 430, based on the recognized intensity of the aerosol or fog, and/or on the basis of the time during which the aerosol or fog is recognized, a debounce time t_fog is determined that is to be allowed to pass after a change of the recognized intensity of the aerosol before the headlamp control unit changes a state of illumination, for example from high beams to low beams or from low beams to high beams. In this way, a change of the state of illumination by the driver as too fast can be avoided, which could possibly irritate the driver and could thus cause dangerous driving situations. Thus, if in a subsequent step 440 fog or the aerosol is no longer recognized, then in a subsequent step 450 the indicated debounce time is allowed to pass, and in a further subsequent step 460 a changeover back to high beams takes place.

According to another application, the present invention can also be used in an adaptive high beam control system AHC as a driver assistance system. Similarly to the controlling of the high and low beams, in the AHC assistance function switching continually takes place between low beams and high beams. Here, steps for example between low beams and high beams can also be initiated or selected that are chosen as a function of the fog or aerosol intensity in such a way that an illumination results that is optimal for the driver. In the case of a high degree of fog intensity, it is advantageous to select a low light distribution or illumination of the area in front of the vehicle, because the resulting blinding is low but good illumination is still present. Similarly, given low fog intensity the headlamps should have as large an opening angle as possible but should not move into high beam operation, because this causes blinding.

The exemplary embodiments described and shown in the Figures have been selected only as examples. Different exemplary embodiments may be combined with one another in their entirety or with regard to individual features. An exemplary embodiment may also be supplemented by features of another exemplary embodiment.

In addition, method steps according to the present invention may be repeated, and may be executed in a sequence differing from that described.

If an exemplary embodiment includes an "and/or" linkage between a first feature and a second feature, this can be read as meaning that the exemplary embodiment according to one specific embodiment has both the first feature and the second feature, and according to a further specific embodiment has either only the first feature or only the second feature.

What is claimed is:

1. A method for determining an intensity of an aerosol in a field of view of a camera of a vehicle, comprising:
reading in image information of an image taken by the camera;
providing (i) a color indicator value for at least one selected subsection of the image taken by the camera, and (ii) a gradient indicator value, wherein the color indicator value represents a relation between a first parameter and a second parameter, wherein the first parameter represents a value obtained with application of a first color filter to the image information in the at least one selected subsection, and the second parameter represents a value obtained one of (a) without application of a color filter, or (b) with application of a second color filter differing from the first color filter, to the image information in the at least one selected subsection, and wherein the gradient indicator value represents a brightness difference, derived from the image information, of a different image region of the image taken by the camera; and
determining an aerosol intensity value using the color indicator value and the gradient indicator value in order to determine the intensity of the aerosol in the field of view of the camera of the vehicle.

2. The method as recited in claim 1, wherein the aerosol intensity value is determined by a weighted linear combination of the color indicator value and the gradient indicator value.

3. The method as recited in claim 2, further comprising:
before the determination of the aerosol intensity value, at least one of (i) standardizing the color indicator value in a range between two color indicator boundary values, and (ii) standardizing the gradient indicator value in a range between two gradient indicator boundary values.

4. The method as recited in claim 2, wherein one of the first color filter or the second color filter is a color filter which filters out red portions in the image information.

5. The method as recited in claim 2, wherein the aerosol indicator intensity value is represented by a scalar.

6. The method as recited in claim 2, wherein:
the image taken by the camera is segmented into multiple non-overlapping image segments; and
the gradient indicator value is determined using image information from a central image segment of the image taken by the camera, the central image segment being surrounded by the remaining image segments of the image.

7. The method as recited in claim 2, further comprising:
comparing the aerosol intensity value to a predetermined threshold value;
wherein the presence of an intensity of the aerosol critical for roadway traffic in the field of view of the camera of the vehicle is determined when the aerosol intensity value is at a specified relation to the predetermined threshold value.

8. The method as recited in claim 2, further comprising:
modifying a radiation of light by a headlight system of the vehicle in a region of illumination in front of the vehicle, in response to the determined intensity of the aerosol in the field of view of the camera of the vehicle.

9. The method as recited in claim 8, wherein the modification of the radiation of light is achieved by modifying a light radiation parameter as a function of a time of the presence of a specified minimum intensity of the aerosol.

10. The method as recited in claim 8, wherein the modification of the radiation of light includes a modification of light distribution.

11. The method as recited in claim 8, wherein the modification of the radiation of light includes switching a light radiation parameter between different states of illumination.

12. A device for method for determining an intensity of an aerosol in a field of view of a camera of a vehicle, comprising:
an interface for reading in image information of an image taken by the camera;
a unit for providing (i) a color indicator value for at least one selected subsection of the image taken by the camera, and (ii) a gradient indicator value, wherein the color indicator value represents a relation between a first parameter and a second parameter, wherein the first parameter represents a value obtained with application of a first color filter to the image information in the at least one selected subsection, and the second parameter represents a value obtained one of (a) without application of a color filter, or (b) with application of a second color filter differing from the first color filter, to the image information in the at least one selected subsection, and wherein the gradient indicator value represents a brightness difference, derived from the image information, of a different image region of the image taken by the camera; and a unit for determining an aerosol intensity value using the color indicator value and the gradient indicator value in order to determine the intensity of the aerosol in the field of view of the camera of the vehicle.

13. A non-transitory computer-readable data storage medium storing a computer program having program codes which, when executed on a computer, perform a method for determining an intensity of an aerosol in a field of view of a camera of a vehicle, the method comprising:

reading in image information of an image taken by the camera;

providing (i) a color indicator value for at least one selected subsection of the image taken by the camera, and (ii) a gradient indicator value, wherein the color indicator value represents a relation between a first parameter and a second parameter, wherein the first parameter represents a value obtained with application of a first color filter to the image information in the at least one selected subsection, and the second parameter represents a value obtained one of (a) without application of a color filter, or (b) with application of a second color filter differing from the first color filter, to the image information in the at least one selected subsection, and wherein the gradient indicator value represents a brightness difference, derived from the image information, of a different image region of the image taken by the camera; and determining an aerosol intensity value using the color indicator value and the gradient indicator value in order to determine the intensity of the aerosol in the field of view of the camera of the vehicle.

\* \* \* \* \*